(12) United States Patent
Chaturvedula et al.

(10) Patent No.: US 8,592,423 B2
(45) Date of Patent: Nov. 26, 2013

(54) INHIBITORS OF PDE10

(75) Inventors: Prasad V. Chaturvedula, Cheshire, CT (US); S. Roy Kimura, Stamford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/525,976

(22) Filed: Jun. 18, 2012

(65) Prior Publication Data

US 2013/0150371 A1 Jun. 13, 2013

Related U.S. Application Data

(60) Provisional application No. 61/499,360, filed on Jun. 21, 2011.

(51) Int. Cl.
*C07D 487/04* (2006.01)

(52) U.S. Cl.
USPC ....... 514/249; 514/259.31; 544/263; 544/350

(58) Field of Classification Search
USPC .................. 514/249, 259.31; 544/263, 350
See application file for complete search history.

(56) References Cited

U.S. PATENT DOCUMENTS

| 5,693,652 A | 12/1997 | Takase et al. |
| 7,456,200 B2 | 11/2008 | Arora et al. |
| 2007/0060584 A1 | 3/2007 | Chakravarty et al. |
| 2008/0167342 A1 | 7/2008 | Strobel et al. |
| 2010/0016303 A1 | 1/2010 | Ritzen et al. |

FOREIGN PATENT DOCUMENTS

| WO | WO 03/093499 | 11/2003 |
| WO | WO 2011/072695 | 6/2011 |
| WO | WO 2011/110545 | 9/2011 |

OTHER PUBLICATIONS

International Search Report mailed Jul. 26, 2012.
Loughney, K. et al., "Isolation and characterization of PDE10A, a novel human 3', 5'-cyclic nucleotide phosphodiesterase," Gene, vol. 234, pp. 109-117 (1999).
Siuciak, J.A., et al., "Genetic deletion of the striatum-enriched phosphodiesterase PDE10A: Evidence for altered striatal function," Neuropharmacology, vol. 51, pp. 374-385 (2006).
Soderling, S.H., et al., "Isolation and characterization of a dual-substrate phosphodiesterase gene family: PDE10A," Proc. Natl. Acad. Sc. USA, vol. 96, pp. 7071-7076 (Jun. 1999).
Fujishige, K., et al., "Cloning and Characterization of a Novel Human Phosphodiesterase That Hydrolyzes Both cAMP and cGMP (PDE10A)," The Journal of Biological Chemistry, vol. 274, No. 26, pp. 18438-18445 (1999).
Rodefer, J.S., et al., "PDE10A inhibition reverses subchronic PCP-induced deficits in attentional set-shifting in rats," European Journal of Neuroscience, vol. 21, pp. 1070-1076 (2005).
Siuciak, J.A., et al., "Inhibition of the striatum-enriched phosphodiesterase PDE10A: A novel approach to the treatment of psychosis," Neuropharmacology, vol. 51, pp. 386-396 (2006).

*Primary Examiner* — San-Ming Hui
*Assistant Examiner* — Kathrien Cruz
(74) *Attorney, Agent, or Firm* — Pamela A. Mingo; Gary D. Greenblatt

(57) ABSTRACT

PDE10 inhibitors having the general formula (I)

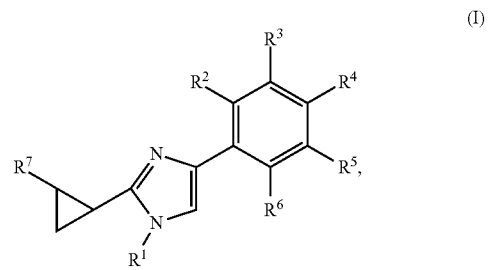

are disclosed. Compositions comprising the compounds and methods for using the compounds to inhibit PDE10 are also disclosed.

10 Claims, No Drawings

INHIBITORS OF PDE10

CROSS-REFERENCE TO RELATED APPLICATIONS

This application claims the benefit of U.S. Provisional Application Ser. No. 61/499,360 filed Jun. 21, 2011.

The present disclosure is generally directed to compounds which inhibit PDE10, compositions comprising such compounds, and methods for inhibiting the function of the PDE10.

Phosphodiesterases (PDEs) are intracellular enzymes that hydrolyze cyclic adenosine monophosphate (cAMP) and cyclic guanosine monophosphate (cGMP) to adenosine monophosphate (AMP) and guanosine monophosphate (GMP), respectively. cAMP and cGMP serve as secondary messengers in several cellular pathways. For example, cAMP and cGMP control activity of cAMP and cGMP-dependent kinases, as well as other proteins with cyclic nucleotide response elements, which in turn controls levels of phosphorylation of proteins that are involved in cellular signaling processes. In neurons, cAMP and cGMP levels impact key neuronal functions such as synaptic transmission, neuronal differentiation, and survival. PDEs are critical regulators of cellular processes because they hydrolyze cAMP and cGMP, thereby generating inactive monophosphates Inhibitors of PDEs will result in increased levels of cAMP and/or cGMP, thereby enhancing levels of signaling.

To date, 11 PDE families have been identified based on their amino acid sequences, catalytic and regulatory characteristics, and sensitivity to small molecule inhibitors. Some PDEs utilize cAMP as a substrate, some hydrolyze cGMP, and some PDEs hydrolyze both cAMP and cGMP. Most PDEs have widespread expression while some are more tissue-specific. As a result of their distinct enzymatic activities and localization, PDEs (and subtypes within families) can serve distinct physiological functions. PDE10 was reported in 1999 (K. Fujishige et al, J. Biol. Chem. 1999, 274, pages 18438-18445; K. Loughney et al, Gene 1999, 234, pages 109-117; S. H. Soderling et al, Proc. Natl. Acad. Sci. USA 1999, 96, pages 7071-7076). PDE10 is a dual substrate PDE that hydrolyzes both cAMP and cGMP. The expression of PDE10 is highest in the brain, particularly in the medium spiny neurons (MSN) of the striatum. The striatal medium spiny neurons are the first input site of the basal ganglia circuit function. The tissue distribution of PDE10 indicates that PDE10 inhibitors can be used to raise levels of cAMP and/or cGMP within cells that express PDE10 in the brain. PDE10 has low levels of expression in the periphery suggesting a reduced propensity for peripheral side effects.

PDE10 KO animals exhibit an antipsychotic phenotype in multiple models thought to be predictive of antipsychotic activity. Additionally, multiple PDE10 inhibitors, that span multiple chemotypes, produce antipsychotic-like behavioral activity (for a review, see T. Chappie et al in Current Opinion in Drug Discovery & Development 2009, 12, pages 458-467). For example, the PDE10 inhibitor papaverine has been shown to be active in several antipsychotic models (WO 03/093499, J. A. Siuciak et al Neuropharmacology, 2006, 51, pages 386-396; J. A. Siuciak et al, Neuropharmacology 2006, 51, pages 374-385). PDE10 inhibitors also exhibit efficacy in models of cognition (for example, J. S. Rodefer et al, Eur. J. Neurosci., 2005, 21, pages 1070-1076). U.S. Pat. No. 5,693,652 discloses a method for treating certain neurologic and psychiatric disorders with the selective PDE10 inhibitor papaverine.

The localization of PDE10 in the brain suggests that PDE10 inhibitors would be useful in the treatment of psychiatric and neurological diseases. These diseases include but are not limited to schizophrenia; positive, negative, and/or cognitive symptoms associated with schizophrenia; delusional disorder; substance-induced psychotic disorder; anxiety disorders such as panic disorder, obsessive-compulsive disorder, acute stress disorder or generalized anxiety disorders; drug addiction; movement disorders such as Parkinson's disease, Huntington's disease or restless leg syndrome; cognition deficiency disorders such as Alzheimer's disease or multi-infarct dementia; mood disorders such as depression or bipolar disorders; or neuropsychiatric diseases such as psychosis, attention-deficit/hyperactivity disorder or related attentional disorders.

The compounds of the present disclosure are PDE10 inhibitors for the treatment of the above-mentioned psychiatric and neurological disorders.

In its first aspect the present disclosure provides a compound of formula (I)

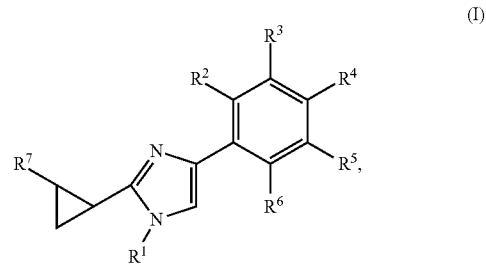

or a pharmaceutically acceptable salt thereof, wherein $R^1$ is selected from hydrogen, $C_1$-$C_6$ alkyl; $C_1$-$C_6$ alkyl($C_3$-$C_8$)cycloalkyl; $C_1$-$C_6$ hydroxyalkyl; $CH_2CN$; $CH_2C(O)NH_2$; $C_1$-$C_6$ arylalkyl; and $C_1$-$C_6$ alkylheterocyclylalkyl;

$R^2$-$R^6$ are independently selected from hydrogen, $C_1$-$C_6$ alkoxy; and halo; and $R^7$ is a heteroaromatic group of formula (II) containing from 2 to 4 nitrogen atoms:

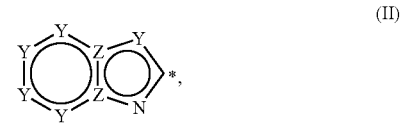

wherein:

each Y is independently N or CH; and each Z is independently N or C; and wherein the heteroaromatic group may be optionally substituted with one, two, or three substitutents independently selected from $C_1$-$C_6$ alkoxy; $C_1$-$C_6$ alkyl; aryl; cyano; halo; halo($C_1$-$C_6$)alkyl; and $C_1$-$C_6$ hydroxyalkyl; and wherein * denotes the point of attachment to the cyclopropyl ring.

In a first embodiment of the first aspect the present disclosure provides a compound of formula (I), or a pharmaceutically acceptable salt thereof, wherein $R^1$ is $C_1$-$C_6$ alkyl. In a second embodiment $R^2$-$R^6$ are hydrogen. In a third embodiment, $R^7$ is selected from

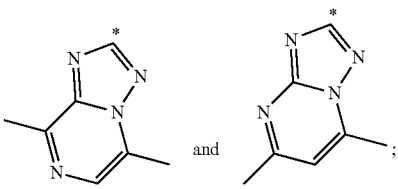

wherein * denotes the point of attachment to the cyclopropyl ring.

In a second aspect the present disclosure provides a composition comprising a compound of formula (I), or a pharmaceutically acceptable salt thereof, and a pharmaceutically acceptable carrier.

In a third aspect the present disclosure provides a method of treating a disorder selected from schizophrenia; positive, negative, and/or cognitive symptoms associated with schizophrenia; delusional disorder; substance-induced psychotic disorder; panic disorder; obsessive-compulsive disorder; acute stress disorder; generalized anxiety disorders; drug addiction; Parkinson's disease; Huntington's disease; restless leg syndrome; Alzheimer's disease; multi-infarct dementia; depression; bipolar disorders; psychosis, and attention-deficit/hyperactivity disorder in a patient, comprising administering to the patient a therapeutically effective amount of a compound of formula (I), or a pharmaceutically acceptable salt thereof. In a first embodiment of the third aspect, the disorder is schizophrenia.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "$C_1$-$C_6$ alkoxy," as used herein, refers to a $C_1$-$C_6$ alkyl group attached to the parent molecular moiety through an oxygen atom.

The term "$C_1$-$C_6$ alkyl," as used herein, refers to a group derived from a straight or branched chain saturated hydrocarbon containing from one to six carbon atoms.

The term "$C_1$-$C_6$ alkyl($C_3$-$C_8$)cycloalkyl" refers to a $C_3$-$C_8$ cycloalkyl which is attached to the parent molecular moiety through a $C_1$-$C_6$ alkyl group.

The term "$C_1$-$C_6$ alkylheterocycloalkyl," as used herein, refers to a heterocycloalkyl group attached to the parent molecular moiety through a $C_1$-$C_6$ alkyl group.

The term "$C_1$-$C_6$ arylalkyl," as used herein, refers to an aryl group attached to the parent molecular moiety through a $C_1$-$C_6$ alkyl group.

The term "aryl," as used herein, refers to a phenyl ring, optionally substituted with halogen, $C_1$-$C_6$ alkyl, $C_1$-$C_6$ alkoxy, or halo($C_1$-$C_6$)alkyl.

The term "cyano," as used herein, refers to —CN.

The term "cycloalkyl," as used herein, refers to a saturated monocyclic or bicyclic hydrocarbon ring system having three to eight carbon atoms and zero heteroatoms. Representative examples of cycloalkyl groups include, but are not limited to, cyclopropyl, cyclobutyl, and cyclopentyl.

The terms "halo" and "halogen," as used herein, refer to F, Cl, Br, and I.

The term "halo($C_1$-$C_6$)alkyl," as used herein, refers to a $C_1$-$C_6$ alkyl group substituted with one, two, or three halogen atoms.

The term "heterocycloalkyl," as used herein, refers to a four- to eight-membered ring containing carbon atoms and up to three atoms selected from N, O, and S, rovided the four- to eight-membered ring does not contain adjacent O or adjacent S atoms.

The term "hydroxy," as used herein, refers to —OH.

The term "$C_1$-$C_6$ hydroxyalkyl," as used herein, refers to a $C_1$-$C_6$ alkyl group substituted with one hydroxy group.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18th ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Asymmetric centers exist in the compounds of the present disclosure. It should be understood that the disclosure encompasses all stereochemical forms, or mixtures thereof, which possess the ability to inhibit PDE10.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of the disorders described herein. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: Et for ethyl; Ph for phenyl; OAc for acetate; DMF for N,N-dimethylformamide; THF for tetrahydrofuran; MeOH for methanol; TBTU for (N,N,N',N'-tetramethyl-O-(benzotriazol-1-yl)uronium tetrafluoroborate; Et$_3$N for triethylamine; TFA for trifluoroacetic acid; rt or RT or Rt for retention time or room temperature (context will dictate); h for hours; min for minutes; and EtOAc for ethyl acetate.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The compounds described in the present disclosure can be prepared readily according to the Scheme 1 or modifications thereof using readily available starting materials, reagents and conventional synthetic procedures. In these reactions, it is also possible to make use of variations which are themselves known to those of ordinary skill in the art, but not described in greater detail.

Commercially available ethyl 2-formyl-1-cyclopropanecarboxylate (98% predominantly trans, Aldrich) was treated with 2-oxo-2-phenylacetaldehyde hydrate and ammonium acetate in methanol provided ethyl 2-(4-phenyl-1H-imidazol-2-yl)cyclopropanecarboxylate in 78% yield. The imidazole moiety was alkylated regioselectively with various alkyl halides mediated by potassium carbonate in DMF to give alkylated products in 30-70% yield. The ester functionality was hydrolyzed with lithium hydroxide under standard conditions. The acid was coupled to either 1-amino-3,6-dimethylpyrazin-2(1H)-iminium 2,4,6-trimethylbenzenesulfonate or 1-amino-4,6-dimethylpyrimidin-2(1H)-iminium 2,4,6-trimethylbenzenesulfonate mediated by O-benzotriazol-1-yl-N,N,N',N'-tetramethyluronium tetrafluoroborate (TBTU) and triethylamine to give the desired products in >40% yield. In this synthetic scheme, it is possible to make variations by using different substituted aminopyrazin-2(1H)-iminium, substituted aminopyrimidin-2(1H)-iminium or substituted 2-aminopyridinium salts of 2,4,6-trimethylbenzenesulfonate to provide several analogs.

DESCRIPTION OF SPECIFIC EMBODIMENTS

In the following examples, all temperatures are given in degrees Centigrade. Proton magnetic resonance ($^1$H NMR) spectra were recorded on a Bruker AC 400 or AC 500. All spectra were determined in the solvents indicated and chemical shifts are reported in δ units downfield from the internal standard tetramethylsilane (TMS) and interproton coupling constants are reported in Hertz (Hz). Splitting pattererns are designated as follows: s, singlet; d, doublet; t, triplet; q, quartet; m, multiplet; br, broad peak. Low resolution mass spectra (MS) and the apparent molecular (MH$^+$) or (M–H)$^+$ was determined on a Waters mass detector 3100 platform. The retention time (R$_t$) was determined on a Shimadzu liquid chromatograph (Model LC-10AT) using Phenomenex Luna

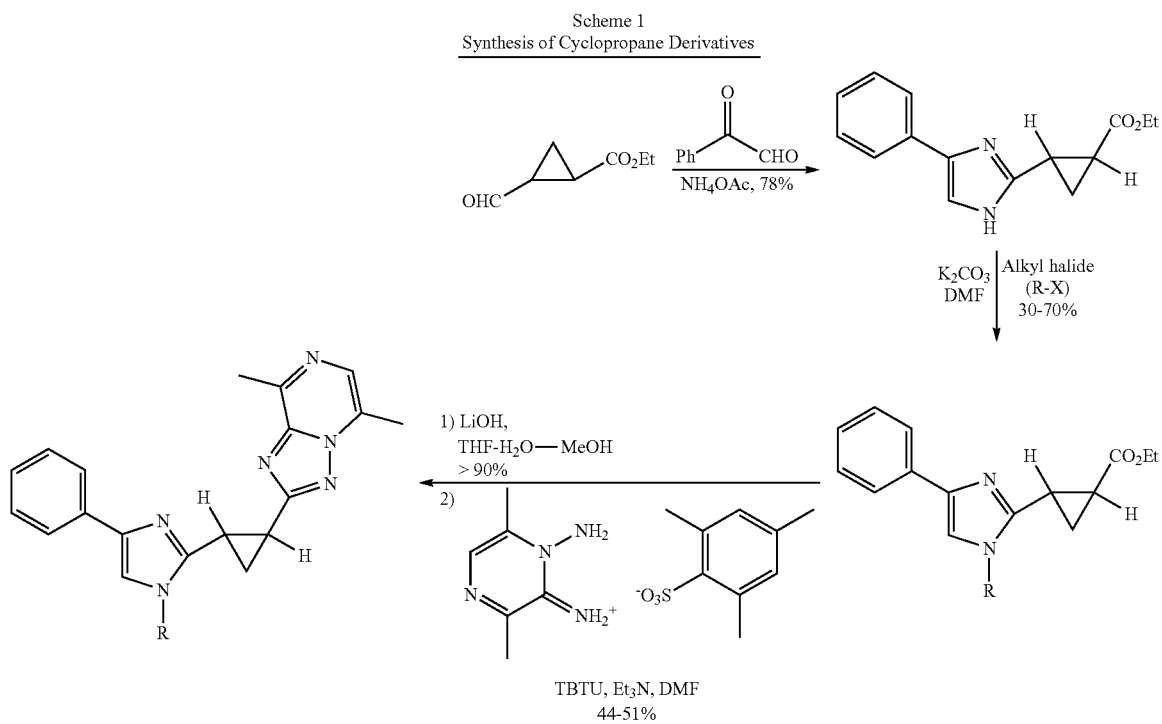

C18 column starting from solvent composition of 95% water/5% acetonitrile/10 mM ammonium acetate ending with a solvent composition of 5% water/95% acetonitrile/10 mM ammonium acetate over a 2 min gradient and 3 min total run time (Condition A). The products were purified by PrepHPLC using either the Waters C18 column (30×100 mm) or Luna Axia C18 column (30×100 mm) at a flow rate of 40.0 mL/min and gradient time of 12.0 min. starting from solvent composition of 10% MeOH-90% $H_2O$-0.1% TFA and ending with solvent composition 90% MeOH-10% $H_2O$-0.1% TFA. Pure fractions were collected and solvent removed under reduced pressure.

Synthesis of Intermediates and Products

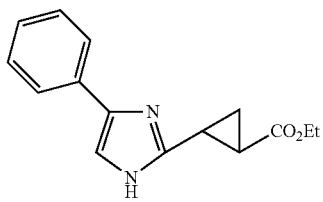 [SMILES: CCOC(=O)C1CC1c1nc(-c2ccccc2)c[nH]1]

Ethyl 2-(4-phenyl-1H-imidazol-2-yl)cyclopropanecarboxylate

To a solution of 2-oxo-2-phenylacetaldehyde, hydrate (3.04 g, 20 mmol) in methanol (35 mL) was added ethyl 2-formyl-1-cyclopanecarboxylate (2.65 mL, 20.00 mmol) followed by ammonium acetate (7.71 g, 100 mmol) at rt. The reaction mixture was stirred at rt for 15 h. Removed solvent and diluted with dichloromethane (150 mL) and washed with water. Removed solvent and purified the crude viscous oil by flash chromatography using 25% EtOAc in hexane to 40% EtOAc in hexane. Collected the pure fractions and removed solvent. Obtained white solid of ethyl 2-(4-phenyl-1H-imidazol-2-yl)cyclopropanecarboxylate (4.0 g, 15.61 mmol, 78% yield). $^1$H NMR (500 MHz, CHLOROFORM-d) δ 7.64 (d, J=7.3 Hz, 2H), 7.39-7.34 (m, 2H), 7.26-7.22 (m, 1H), 7.19 (s, 1H), 4.17 (qd, J=7.1, 0.7 Hz, 2H), 2.52 (ddd, J=9.2, 6.2, 4.1 Hz, 1H), 2.29-2.24 (m, 1H), 1.69 (ddd, J=8.5, 6.3, 4.3 Hz, 1H), 1.58 (ddd, J=9.3, 5.3, 4.3 Hz, 1H), 1.31-1.26 (m, 3H); MS (ESI) 257 (M+H); $R_f$=1.63 (Condition A).

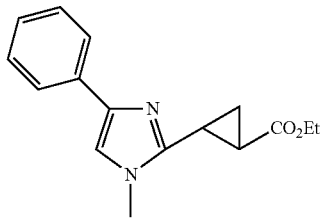 [SMILES: CCOC(=O)C1CC1c1nc(-c2ccccc2)cn1C]

Ethyl 2-(1-methyl-4-phenyl-1H-imidazol-2-yl)cyclopropanecarboxylate

To a solution of ethyl 2-(4-phenyl-1H-imidazol-2-yl)cyclopropanecarboxylate (1025 mg, 4 mmol) in DMF (5 mL) was added potassium carbonate (608 mg, 4.40 mmol) followed by iodomethane (0.275 mL, 4.40 mmol) at rt. The reaction mixture was heated at 50° C. for 12 h. Cooled and diluted with ether (30 mL) and washed with water, brine and dried ($Na_2SO_4$). TLC (25% EtOAc in hexane) showed presence of starting material (10-20%). Purified by flash chromatography using 25% EtOAc in hexane to give pure ethyl 2-(1-methyl-4-phenyl-1H-imidazol-2-yl)cyclopropanecarboxylate (746 mg, 2.62 mmol, 65.5% yield). The ester solidified to a white solid over a period of time. $^1$H NMR (500 MHz, CHLOROFORM-d) δ 7.79-7.61 (m, 2H), 7.43-7.27 (m, 2H), 7.24-7.14 (m, 1H), 7.02 (s, 1H), 4.20 (q, J=7.2 Hz, 2H), 3.61 (s, 3H), 2.42 (ddd, J=9.0, 6.2, 4.0 Hz, 1H), 2.29 (ddd, J=8.5, 5.3, 4.1 Hz, 1H), 1.69 (ddd, J=8.5, 6.1, 4.0 Hz, 1H), 1.59 (ddd, J=9.1, 5.3, 3.9 Hz, 1H), 1.30 (t, J=7.1 Hz, 3H); MS (ESI) 271 (M+H); $R_f$=1.90 (Condition A).

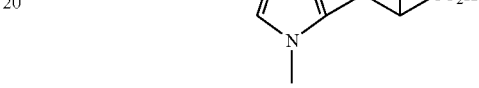

2-(1-Methyl-4-phenyl-1H-imidazol-2-yl)cyclopropanecarboxylic acid

To a solution of ethyl 2-(1-methyl-4-phenyl-1H-imidazol-2-yl)cyclopropanecarboxylate (746 mg, 2.76 mmol) in tetrahydrofuran (15 mL) was added lithium hydroxide monohydrate (232 mg, 5.52 mmol) in water (5.00 mL) at rt. Added methanol (5.00 mL) and stirred for 15 h at rt. Removed solvent. Obtained a white solid. Redissolved in water (15 mL) and neutralized with 5.5 mL of 1.0 M HCl. Removed solvent and azetroped with toluene (2×10 mL). Dried for 20 h and obtained 2-(1-methyl-4-phenyl-1H-imidazol-2-yl)cyclopropanecarboxylic acid as a white powder. MS (ESI) 243 (M+H); $R_f$=1.35 (Condition A).

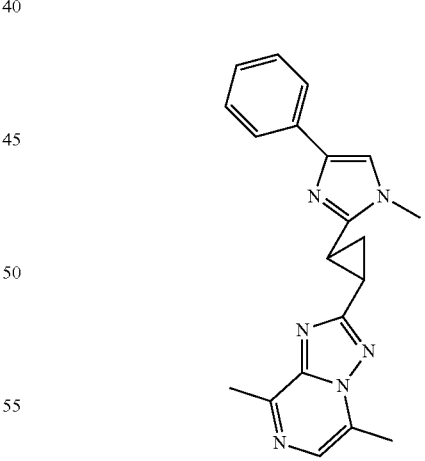

5,8-Dimethyl-2-(2-(1-methyl-4-phenyl-1H-imidazol-2-yl)cyclopropyl)-[1,2,4]triazolo[1,5-a]pyrazine To a solution of 2-(1-methyl-4-phenyl-1H-imidazol-2-yl)cyclopropanecarboxylic acid (70 mg, 0.289 mmol) in DMF (2.0 mL) was added 1-amino-3,6-dimethylpyrazin-2(1H)-iminium 2,4,6-trimethylbenzenesulfonate (98 mg, 0.289 mmol) followed by O-benzotriazol-1-yl-N,N,N',N'-tetramethyluronium tetrafluoroborate (93 mg, 0.289 mmol) and triethylamine (0.040 mL, 0.289 mmol) at rt. After 2 h stirring at rt, the reaction mixture was stirred at 70° C. for 12 h. The crude was purified by prep HPLC using Phenomenex column and MeOH—H₂O-TFA as eluent (20% to 100% over 12 min gradient; flow: 40 mL/min). Collected the pure fractions and removed solvent. Obtained 5,8-dimethyl-2-(2-(1-methyl-4-phenyl-1H-imidazol-2-yl)cyclopropyl)-[1,2,4]triazolo[1,5-a]pyrazine in 44% yield. Prepared hydrochloride salt by adding 1.0 M HCl (3 mL) and MeOH (3 mL) and removing solvent. ¹H NMR (500 MHz, METHANOL-d₄) δ 6.63 (s, 1H), 6.24 (s, 1H), 6.15-6.11 (m, 2H), 5.90-5.85 (m, 2H), 5.84-5.79 (m, 1H), 2.33 (s, 3H), 1.74-1.71 (m, 1H), 1.50-1.44 (m, 4H), 1.28 (s, 3H), 0.63-0.58 (m, 1H), 0.56-0.51 (m, 1H); MS (ESI) 345 (M+H); R$_f$=1.61 (Condition A).

The racemic 5,8-dimethyl-2-(2-(1-methyl-4-phenyl-1H-imidazol-2-yl)cyclopropyl)-[1,2,4]triazolo[1,5-a]pyrazine was separated into individual enantiomers by SFC method using an isocratic mobile phase (30% Ethanol with 0.1% Diethylamine and 70% CO2) on a chiral SFC Chiralcel OJ-H column (4.6×250 mm, 5 μm) at 35° C., 150 bar pressure and at a flow rate of 2 mL/min. The retention times of individual enantiomers were 13.87 min and 18.26 min.

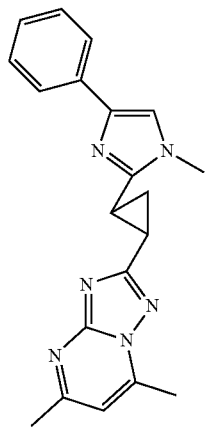 [SMILES: Cc1cc(C)n2nc(C3CC3c3nc(-c4ccccc4)cn3C)nc2n1]

5,7-Dimethyl-2-(2-(1-methyl-4-phenyl-1H-imidazol-2-yl)cyclopropyl)-[1,2,4]-triazolo[1,5-a]pyrimidine To a solution of 2-(1-methyl-4-phenyl-1H-imidazol-2-yl)cyclopropanecarboxylic acid (70 mg, 0.289 mmol) in DMF (2.0 mL) was added 1-amino-4,6-dimethylpyrimidin-2(1H)-iminium 2,4,6-trimethylbenzenesulfonate (98 mg, 0.289 mmol) followed by O-benzotriazol-1-yl-N,N,N',N'-tetramethyluronium tetrafluoroborate (93 mg, 0.289 mmol) and triethylamine (0.040 mL, 0.289 mmol) at rt. After 2 h stirring at rt, the reaction mixture was stirred at 70° C. for 12 h. The crude product was purified by prep HPLC using Phenomenex column and MeOH—H₂O-TFA as eluent (20% to 100% over 12 min gradient; flow: 40 mL/min) Collected the pure fractions and removed solvent. Obtained 5,7-dimethyl-2-(2-(1-methyl-4-phenyl-1H-imidazol-2-yl)cyclopropyl)-[1,2,4]triazolo[1,5-a]pyrimidine as a white solid in 47% yield. Prepared hydrochloride salt by adding 1.0 M HCl and MeOH and removing solvent. ¹H NMR (500 MHz, METHANOL-d₄) δ 6.28 (s, 1H), 6.18-6.14 (m, 2H), 5.97 (s, 1H), 5.92-5.88 (m, 2H), 5.87-5.84 (m, 1H), 2.39 (s, 3H), 1.72-1.69 (m, 1H), 1.62-1.57 (m, 1H), 1.29-1.27 (m, 3H), 1.17 (s, 3H), 0.70 (dt, J=9.2, 6.1 Hz, 1H), 0.62-0.59 (m, 1H); MS (ESI) 345 (M+H); R$_f$=1.84 (Condition A).

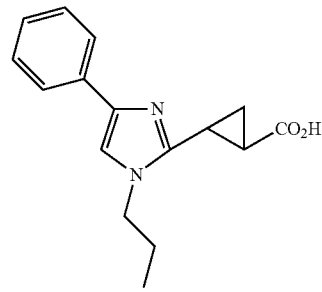 [SMILES: CCCn1cc(-c2ccccc2)nc1C1CC1C(=O)O]

2-(4-Phenyl-1-propyl-1H-imidazol-2-yl)cyclopropanecarboxylic acid

To a solution of ethyl 2-(4-phenyl-1H-imidazol-2-yl)cyclopropanecarboxylate in DMF (3.0 mL) was added 1-iodopropane followed by potassium carbonate. The reaction mixture was heated at 70° C. for 12 h. Cooled and diluted with ether (50 mL). Washed with water, brine and dried (Na₂SO₄). The crude was purified by flash chromatography using 25% EtOAc in hexane to give the alkylated N-propyl product in 30% yield. Dissolved the N-propyl product in tetrahydrofuran (10.00 mL) and added lithium hydroxide (0.016 g, 0.66 mmol) in water (3.00 mL) and methanol (3.00 mL). Stirred for 12 h at rt. Removed solvent and added 1.0 M HCl (0.66 mL) and removed solvent. Azetroped with toluene (2×5 mL) and dried. The carboxylic acid was obtained as a white powder. ¹H NMR (500 MHz, CHLOROFORM-d) δ 7.74-7.70 (m, 2H), 7.36-7.32 (m, 2H), 7.20 (tt, J=7.3, 1.3 Hz, 1H), 7.10 (s, 1H), 4.24-4.16 (m, 2H), 3.94 (t, J=7.2 Hz, 2H), 2.43 (ddd, J=9.1, 6.2, 4.0 Hz, 1H), 2.32-2.27 (m, 1H), 1.84 (sxt, J=7.3 Hz, 2H), 1.74 (ddd, J=8.5, 6.3, 4.0 Hz, 1H), 1.60 (ddd, J=9.2, 5.3, 4.0 Hz, 1H), 1.30 (t, J=7.1 Hz, 3H), 0.98 (t, J=7.4 Hz, 3H); MS (ESI) 299 (M+H); R$_f$=1.91 (Condition A).

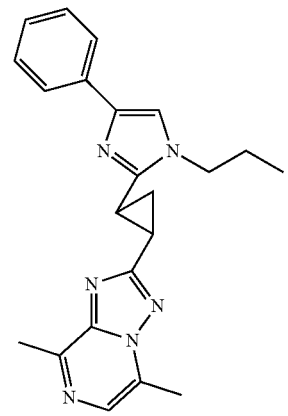 [SMILES: CCCn1cc(-c2ccccc2)nc1C1CC1c1nc2c(C)ncc(C)n2n1]

5,8-Dimethyl-2-(2-(4-phenyl-1-propyl-1H-imidazol-2-Acyclopropyl)-[1,2,4]triazolo[1,5-a]pyrazine To a solution of 2-(4-phenyl-1-propyl-1H-imidazol-2-yl)cyclopropanecarboxylic acid (56.8 mg, 0.21 mmol) in DMF (3.0 mL) was added 1-amino-3,6-dimethylpyrazin-2(1H)-iminium 2,4,6-trimethylbenzenesulfonate (71.1 mg, 0.210 mmol) followed by O-benzotriazol-1-yl-N,N,N',N'-tetramethyluronium tetrafluoroborate (67.4 mg, 0.210 mmol) and triethylamine (0.146 mL, 1.050 mmol) at rt. After 1 h stirring at rt, the reaction mixture was heated at 70° C. for 15 h. The crude was purified by prep HPLC using Phenomenex column and MeOH—$H_2O$-TFA as eluent (25% to 100% over 12 min gradient; 40 mL/min flow). Collected the pure fractions and removed solvent. Obtained 5,8-dimethyl-2-(2-(4-phenyl-1-propyl-1H-imidazol-2-yl)cyclopropyl)-[1,2,4]triazolo[1,5-a]pyrazine, 1.0HCl (44 mg, 0.103 mmol, 49.2% yield) as a white solid after the addition of 1.0 M HCl (3 mL) and methanol (3 mL) followed by removal of solvent. $^1$H NMR (500 MHz, METHANOL-$d_4$) δ 8.15 (d, J=0.9 Hz, 1H), 7.98 (s, 1H), 7.79 (d, J=1.5 Hz, 1H), 7.78-7.77 (m, 1H), 7.58-7.54 (m, 2H), 7.52 (d, J=7.2 Hz, 1H), 4.30 (m, 2H), 3.29-3.26 (m, 1H), 3.08-3.06 (m, 1H), 3.01 (s, 3H), 2.86 (s, 3H), 2.23-2.19 (m, 2H), 2.02 (m, 2H), 1.05 (t, J=7.4 Hz, 3H); MS (ESI) 373 (M+H); $R_f$=2.07 (Condition A).

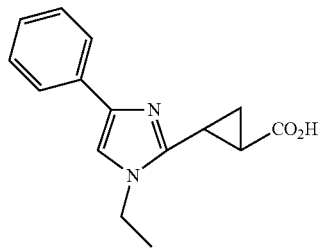 [SMILES: CCn1cc(-c2ccccc2)nc1C1CC1C(=O)O]

2-(1-Ethyl-4-phenyl-1H-imidazol-2-yl)cyclopropanecarboxylic acid

To a solution of ethyl 2-(4-phenyl-1H-imidazol-2-yl)cyclopropanecarboxylate (0.256 g, 1 mmol) in DMF (3.0 mL) was added iodoethane (0.172 g, 1.100 mmol) followed by potassium carbonate (0.152 g, 1.100 mmol). The reaction mixture was heated at 70° C. for 12 h. Cooled and diluted with ether (50 mL). Washed with water, brine and dried ($Na_2SO_4$). The crude product was purified by flash chromatography using 25% EtOAc in hexane to give the alkylated N-ethyl product in 60% yield). Dissolved the alkylated N-ethyl product in tetrahydrofuran (10.00 mL) and added lithium hydroxide (0.029 g, 1.200 mmol) in water (3.00 mL) and methanol (3.00 mL). Stirred for 12 h at rt. Removed solvent and added 1.0 M HCl (1.2 mL) and removed solvent. Azetroped with toluene (2×5 mL) and dried. $^1$H NMR (500 MHz, CHLOROFORM-d) δ 7.73-7.69 (m, 2H), 7.37-7.31 (m, 2H), 7.20 (tt, J=7.4, 1.2 Hz, 1H), 7.12 (s, 1H), 4.24-4.17 (m, 2H), 4.03 (q, J=7.3 Hz, 2H), 2.43 (ddd, J=9.1, 6.2, 4.0 Hz, 1H), 2.33-2.27 (m, 1H), 1.73 (ddd, J=8.5, 6.3, 4.0 Hz, 1H), 1.60 (ddd, J=9.1, 5.3, 4.0 Hz, 1H), 1.47-1.43 (m, 3H), 1.30 (t, J=7.2 Hz, 3H); MS (ESI) 285 (M+H); $R_f$=1.87 (Condition A).

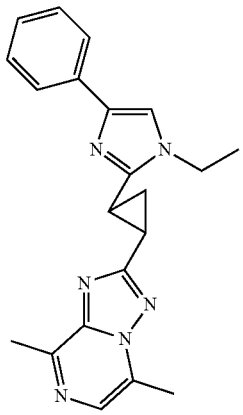 [SMILES: CCn1cc(-c2ccccc2)nc1C1CC1c1nc2c(C)ncc(C)n2n1]

2-(2-(1-Ethyl-4-phenyl-1H-imidazol-2-yl)cyclopropyl)-5,8-dimethyl-[1,2,4]triazolo[1,5-a]pyrazine To a solution of 2-(1-ethyl-4-phenyl-1H-imidazol-2-yl)cyclopropanecarboxylic acid (103 mg, 0.4 mmol) in DMF (3.0 mL) was added 1-amino-3,6-dimethylpyrazin-2(1H)-iminium 2,4,6-trimethylbenzenesulfonate (135 mg, 0.400 mmol) followed by O-benzotriazol-1-yl-N,N,N',N'-tetramethyluronium tetrafluoroborate (128 mg, 0.400 mmol) and triethylamine (0.277 mL, 2.000 mmol) at rt. After 1 h stirring at rt, the reaction mixture was heated at 70° C. for 15 h. The crude was purified by prep HPLC using Phenomenex column and MeOH—$H_2O$-TFA as eluent (25% to 100% over 12 min gradient; 40 mL/min flow). Collected the pure fractions and removed solvent. Prepared HCl salt by adding MeOH (3 mL) and 1.0 M HCl (3 mL) and removing solvent. Obtained 2-(2-(1-ethyl-4-phenyl-1H-imidazol-2-yl)cyclopropyl)-5,8-dimethyl-[1,2,4]triazolo[1,5-a]pyrazine, 1.0HCl (85 mg, 0.202 mmol, 50.6% yield) as a white solid. $^1$H NMR (500 MHz, METHANOL-$d_4$) δ 8.13 (d, J=0.9 Hz, 1H), 7.99 (s, 1H), 7.80-7.78 (m, 1H), 7.77-7.75 (m, 1H), 7.58-7.50 (m, 2H), 7.40-7.22 (m, 1H), 4.38 (q, J=7.3 Hz, 2H), 3.29-3.25 (m, 1H), 3.10-3.08 (m, 1H), 2.98 (s, 3H), 2.85 (s, 3H), 2.21-2.18 (m, 2H), 1.60 (t, J=7.4 Hz, 3H); MS (ESI) 359 (M+H); $R_f$=1.99 (Condition A).

BIOLOGICAL STUDIES

LE_PDE10A Inhibition Assay:

The PDE10 inhibition assay in 384-well plates was conducted to identify substances for the inhibition of cyclic nucleotide hydrolysis by the PDE10 enzyme. The cyclic nucleotide substrate concentration used was at a $K_m$ concentration (25 nM final). PDE10 activity was measured using Scintillation Proximity Assay (SPA)-based methods. PDE10 catalyses the hydrolysis of the intracellular messenger adenosine 5',8'-cyclic phosphate (cAMP) to the non-cyclic adenosine 5'-monophosphate (AMP). The SPA assay was based upon the selective interaction of the tritiated product with yttrium oxide LEADseeker beads.

The assay was performed in 10 μL samples containing 5 μL of 0.3 ng/mL PDE10 final and 5 μL of $3^H$-5',8' cAMP (PerkinElmer, NET111540) run at $K_m$ of 25 nM final. The assay buffer contained 25 mM HEPES pH 7.4, 2.5 mM Magnesium Chloride and 0.1% BSA. Compound dose response curves were pre-incubated with 5 L of 2×PDE10 enzyme for 10 minutes prior to adding 5 ul of 2×$K_m$ substrate for 30 minutes. The reaction was terminated by adding 6 μL of 5 mg/mL of yttrium oxide LEADseeker beads. The beads were allowed to settle for 3 hours before plates were read in the LEEDSeaker for 6 minutes. The measured signal ccould be converted to activity relative to an inhibited control (100%). IC50 values were calculated by using in-house data software and IC50 values were generated by nonlinear regression analysis. (Bristol-Myers Squibb Company, Wallingford, Conn.).

Table 1 shows the IC50 values of the compounds of the present disclosure. Ranges are as follows: A=0.8 nM-5 nM; B=5.1 nM-10 nM; C=10.1 nM-40 nM.

TABLE 1

| Structure | Range | IC50 (nM) |
|---|---|---|
| 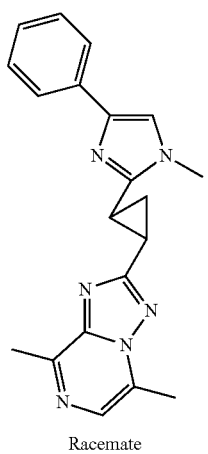 [SMILES: Cc1ncc(C)n2nc(C3CC3c3nc(-c4ccccc4)cn3C)nc12]<br>Racemate | A | 1.79 |
| 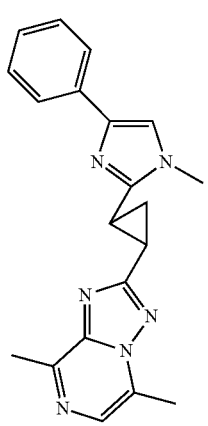<br>Enantiomer 1 | A | |

TABLE 1-continued

| Structure | Range | IC50 (nM) |
|---|---|---|
| 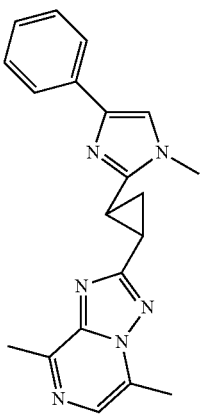<br>Enantiomer 2 | C | |
| 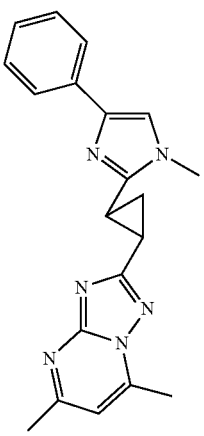 [SMILES: Cc1cc(C)n2nc(C3CC3c3nc(-c4ccccc4)cn3C)nc2n1] | C | 14.52 |
| 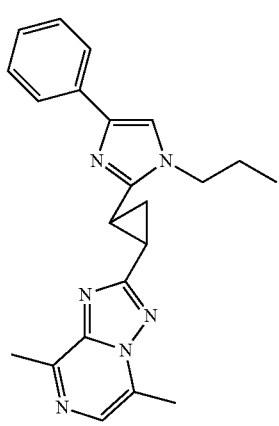 [SMILES: CCCn1cc(-c2ccccc2)nc1C1CC1c1nc2c(C)ncc(C)n2n1] | B | 6.65 |

TABLE 1-continued

| Structure | Range | IC50 (nM) |
|---|---|---|
| 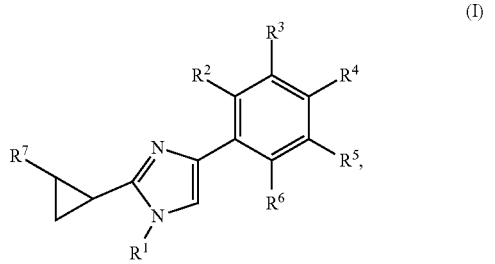 | B | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

(I)

or a pharmaceutically acceptable salt thereof, wherein
$R^1$ is selected from hydrogen, $C_1$-$C_6$ alkyl; $C_1$-$C_6$ alkyl($C_3$-$C_8$)cycloalkyl; $C_1$-$C_6$ hydroxyalkyl; $CH_2CN$; $CH_2C(O)NH_2$; $C_1$-$C_6$ arylalkyl; and $C_1$-$C_6$ alkylheterocyclylalkyl;
$R^2$-$R^6$ are independently selected from hydrogen, $C_1$-$C_6$ alkoxy; and halo; and
$R^7$ is a heteroaromatic group of formula (II) containing from 2 to 4 nitrogen atoms:

(II)

wherein:
each Y is independently N or CH; and
each Z is independently N or C; and wherein the heteroaromatic group may be optionally substituted with one, two, or three substitutents independently selected from $C_1$-$C_6$ alkoxy; $C_1$-$C_6$ alkyl; aryl; cyano; halo; halo($C_1$-$C_6$)alkyl; and $C_1$-$C_6$ hydroxyalkyl; and wherein * denotes the point of attachment to the cyclopropyl ring.

2. A compound of claim 1, or a pharmaceutically acceptable salt thereof, wherein $R^1$ is $C_1$-$C_6$ alkyl.

3. A compound of claim 2, or a pharmaceutically acceptable salt thereof, wherein $R^2$-$R^6$ are hydrogen.

4. A compound of claim 3, or a pharmaceutically acceptable salt thereof, wherein $R^7$ is selected from

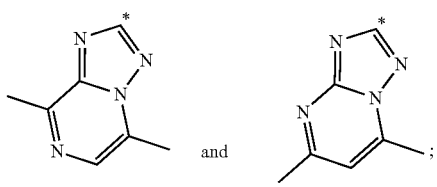

wherein * denotes the point of attachment to the cyclopropyl ring.

5. A compound which is

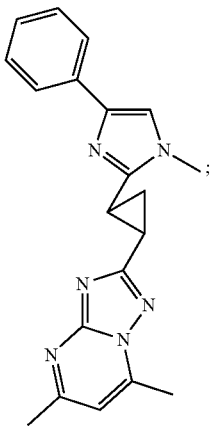 [SMILES: Cc1cc(C)n2nc(C3CC3c3nc(-c4ccccc4)cn3C)nc2n1]

or a pharmaceutically acceptable salt thereof.

6. A compound which is

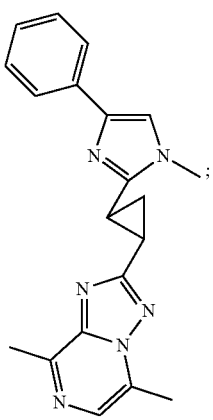 [SMILES: Cc1ncc(C)n2nc(C3CC3c3nc(-c4ccccc4)cn3C)nc12]

or a pharmaceutically acceptable salt thereof.

7. A compound which is

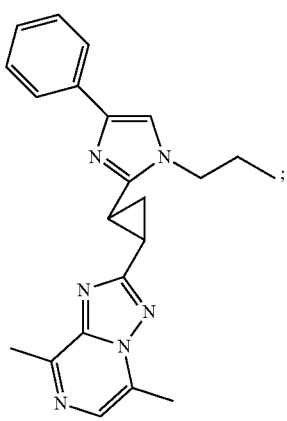 [SMILES: CCCn1cc(-c2ccccc2)nc1C1CC1c1nc2c(C)ncc(C)n2n1]

or a pharmaceutically acceptable salt thereof.

8. A compound which is

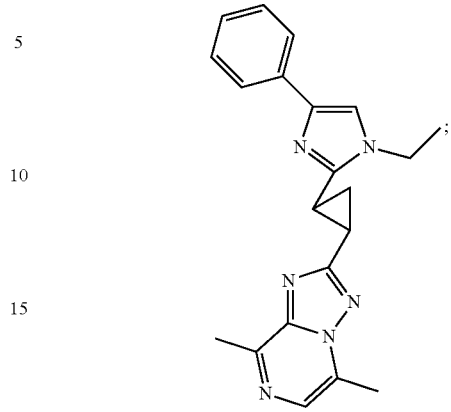

or a pharmaceutically acceptable salt thereof.

9. A composition comprising a compound of claim 1, or a pharmaceutically acceptable salt thereof, and a pharmaceutically acceptable carrier.

10. A method of treating schizophrenia; positive, negative, and/or cognitive symptoms associated with schizophrenia, comprising administering to the patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,592,423 B2
APPLICATION NO. : 13/525976
DATED : November 26, 2013
INVENTOR(S) : Prasad Chaturvedula et al.

It is certified that error appears in the above-identified patent and that said Letters Patent is hereby corrected as shown below:

In the Claims:

Claim 1, col. 19, lines 51-52, delete "alkylheterocyclylalkyl;" and insert -- alkylheterocycloalkyl; --; and Claim 1, col. 20, line 2, delete "substitutents" and insert -- substituents --, therefor.

Signed and Sealed this
Fourteenth Day of October, 2014

Michelle K. Lee
*Deputy Director of the United States Patent and Trademark Office*